(12) United States Patent
MacDonald et al.

(10) Patent No.: US 8,628,710 B2
(45) Date of Patent: *Jan. 14, 2014

(54) PLASTICIZER FOR THERMOPLASTIC POLYMER MATERIALS

(75) Inventors: John Gavin MacDonald, Decatur, GA (US); Teuta Elshani, Woodstock, GA (US); Hristo A. Hristov, Roswell, GA (US); Molly K. Smith, Atlanta, GA (US); Ilona F. Weart, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 789 days.

This patent is subject to a terminal disclaimer.

(21) Appl. No.: 12/635,256

(22) Filed: Dec. 10, 2009

(65) Prior Publication Data

US 2011/0143621 A1 Jun. 16, 2011

(51) Int. Cl.
*B29C 43/22* (2006.01)
*B29D 29/10* (2006.01)

(52) U.S. Cl.
USPC ............ 264/280; 264/231; 264/901; 523/118

(58) Field of Classification Search
USPC ........... 442/181, 286, 394; 264/280, 239, 901
See application file for complete search history.

(56) References Cited

U.S. PATENT DOCUMENTS

| | | |
|---|---|---|
| 3,903,024 A | 9/1975 | Wright |
| 5,504,184 A | 4/1996 | Caruso et al. |
| 6,136,326 A | 10/2000 | Kotzev |
| 6,224,622 B1 | 5/2001 | Kotzev |
| 6,281,310 B1 | 8/2001 | Kotzev |
| 2001/0001690 A1 | 5/2001 | Phillips |
| 2004/0022755 A1 | 2/2004 | Kamath |
| 2008/0161508 A1 | 7/2008 | Matsumoto et al. |
| 2009/0098073 A1 | 4/2009 | MacDonald et al. |
| 2009/0098081 A1 | 4/2009 | MacDonald et al. |

FOREIGN PATENT DOCUMENTS

EP 1580229 A1 9/2005

OTHER PUBLICATIONS

Lillie, R.D., M.D., "Xanrhenes and Acridines," Chapter 13, *H.J. Conn's Biological Stains*, 9th Edition, Williams & Wilkins, 1977, pp. 326-363.

Tsuji, Hideto and Yoshito Ikada, "Blends of Crystalline and Amorphous Poly(lactide). III. Hydrolysis of Solution-Cast Blend Films," *Journal of Applied Polymer Science*, vol. 63, No. 7, Feb. 14, 1997, pp. 855-863.

*Primary Examiner* — Lynda Salvatore
(74) *Attorney, Agent, or Firm* — James B. Robinson; Vincent T. Kung

(57) ABSTRACT

A thermoplastic polymeric composition having a xanthene or xanthenes-based compound as a plasticizer, a method to modify the thermoplastic polymeric materials to increase their relative plasticity while maintaining good strength or "toughness" characteristics, and various articles of manufacture that can be made using the polymer composition are described.

8 Claims, 9 Drawing Sheets

XRD experimental curve of Example #7 after cooling with 10° C/min (curve #1). Curves #2 and #3 are the two amorphous halos and curves #4 and #5 are the two crystalline peaks.

DMA changes of the storage modulus (E') of Control Sample (dashed curve) and and Example #1 (solid curve) after cooling with 10° C/min.

Stress-strain curves @ 40° C of Control Sample (PLA and 10° C/min cooling; solid circles) and Example#1 (PLA+5000ppm DBF and 10° C/min cooling; open circles).

PLASTICIZER FOR THERMOPLASTIC POLYMER MATERIALS

CLAIM OF BENEFIT OF PRIORITY

The present application claims benefit of priority to U.S. patent application Ser. No. 12/340,409, filed on Dec. 19, 2008, now U.S. Pat. No. 8,518,315, the contents of which are incorporated herein.

FIELD OF INVENTION

The present invention pertains to certain chemical additives that can be incorporated into thermoplastic polymeric materials to increase the relative plasticity of the polymeric material. In particular, the present invention relates to the plasticizing effect of xanthenes or xanthene-based molecular structures in semi-crystalline thermoplastic polymers.

BACKGROUND

Molecular shape and the way molecules are arranged in a solid are important factors in determining the macroscopic physical properties of polymers. The relative degree of either brittleness or plasticity of a particular polymer material is dependent on the molecular structure, conformation and orientation of the polymer. The general concept of self-assembly enters into the organization of molecules on the micro and macroscopic scale as they aggregate into more ordered structures. Crystallization of regular solids is an example of the self-assembly process, as is the spatial organization of liquid crystals.

Conventional thermoplastic polymers, such as polypropylene or polylactic acid, tend to be relatively hard and rigid, sometimes even brittle. Manufacturers have over the years tried to develop or modify conventional thermoplastic materials to make them more pliable or "softer," but few have had success. This need for a new material composition or method to modify the thermoplastic polymeric materials to increase their relative amorphous content remains unsatisfied. The present invention provides a plasticizer composition to address this unfulfilled need.

SUMMARY OF THE INVENTION

The present invention pertains to xanthenes and xanthenes-based molecular structures in semi-crystalline thermoplastic polymer that can result in a highly amorphous thermoplastic material composition. The new composition yields a polymer material that is simultaneously softer or more pliable and stronger or tougher than the original or control starting polymer. This feature is a unique and unexpected finding of the composition which offers both benefits. The present invention pertains to, in part, a thermoplastic polymeric composition having a starting base semi-crystalline polymer with a minimal crystalline content of about 14% to about 87% by weight of the polymer, and a plasticizer compound with a xanthene-based molecular structure dispersed among the polymer molecules, in an amount up to about 6000 ppm. When solidified at ambient room temperature, the polymer composition a crystalline phase, and an amorphous phase in a ratio range of about 0-15:85-100, respectively when compared to the starting polymer which has 14-87:13-86 respectively. The plasticizer compound with a xanthene-based molecular structure is dispersed within the amorphous phase. The resulting thermoplastic polymeric composition is essentially amorphous and has a relative level of crystallinity of 40-99% less than that of the starting or a control thermoplastic polymer that does not include the plasticizer compound with a xanthene-based molecular structure therein.

Incorporation of the plasticizer compound into the thermoplastic polymeric composition can increase the relative toughness of the base or underlying thermoplastic polymer by about at least 50%, and the relative tolerance for stretching and elongation by about at least 30%, and increase in the both the strain at break and stress at break by about at least 40% when the samples are analyzed in the temperature range 30-50° C. This would be additional benefit in the use of this composition in absorbent articles and medical devices in contact or inserted into the body.

The semi-crystalline polymer may include members of the polyalkylcarboxylic acids, for example, polylactic acid. The semi-crystalline control polymer can contain a crystalline content of about 14 to about 87% crystalline phase, about 13% to about 86% amorphous state. The plasticizer compound with a xanthene-based molecular structure is present at about 1000 ppm to about 6000 ppm, and may include xanthene and halogenated or mixed-halogenated xanthenes.

In another aspect, the present invention relates to an article of manufacture made with a semi-crystalline thermoplastic polymer matrix that incorporates a plasticizer having a xanthene molecule or a compound with a xanthene-based molecular structure. The article of manufacture can be a film, a fiber, woven fibers, or nonwoven fiber web, absorbent articles (e.g., wipers, diapers, adult incontinence products, feminine pads), garments, protective fabrics and suits (e.g., surgical gowns or drapes, work overalls, dust or chemical protective outfits), wrapper or packaging materials or articles (e.g., diaper bag), face-masks, medical drapes, endotracheal tube, catheters, bladders or balloons, or any other item that may require a certain degree of flexibility or pliability and perceived and yet tougher.

In another aspect, the present invention also pertains to a method of modifying the plasticity of a starting base crystalline-phase-containing thermoplastic polymer. The method involves providing in a mixture a thermoplastic polymer with about 14% to about 87% crystallinity and a plasticizing agent having a xanthene-based molecular structure present in an amount of up to about 1000 ppm to about 6000 ppm of total composition; thoroughly mixing the thermoplastic polymer and said plasticizing agent in a molten or liquid state between a temperature range of about 140-300° C.; and dispersing uniformly the plasticizing agent throughout the molten mixture; and solidifying the molten mixture such that the xanthenes or xanthene-based molecular structure migrates into the mesophase and amorphous phase. When solidified the resulting solid exhibits a crystalline content that is at least 40% less than the underlying or original thermoplastic polymer that was without the plasticizing agent. The method may further involve extruding or forming the molten mixture of the hot plasticized thermoplastic material into variety of solid forms or products when at about ambient room temperature.

Additional features and advantages of the xanthene containing semi-crystalline thermoplastic polymeric compositions will be described in the following detailed description. It is understood that the foregoing general description and the following details description and examples are merely representative of the invention, and are intended to provide an overview for understanding the invention as claimed.

DETAILED DESCRIPTION OF THE INVENTION

Section I

Definitions

Figure 1:
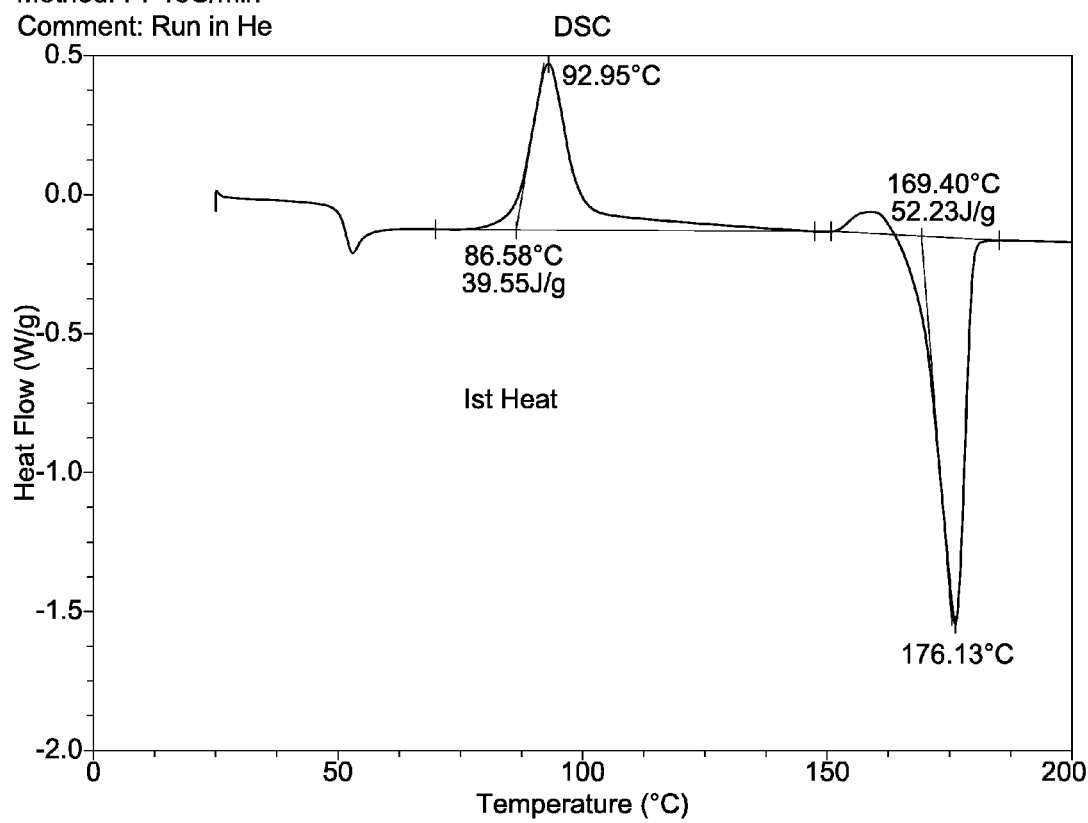
FIG. 1 shows a graph of the DSC curve of Control Sample (PLA control—solution cast); first heat.

In general, the present invention pertains to thermoplastic polymer compositions that are modified with a plasticizing compound containing a xanthene or xanthene-based molecular structure.

As used herein, the term "thermoplastic polymer" or "thermoplastic material" refers to an organic macromolecule composed of a large number of monomers, with molecular weight that may range from about 5,000 into the hundreds of thousands, which softens when exposed to heat and returns to its original condition when cooled to room temperature, such as polyalkylcarboxylic acids and more specifically polylactic acid.

As used herein, a "plasticizer," "plasticizing agent," or "plasticizing compound" is an organic compound that is added to a thermoplastic polymer which can both facilitate processing and increase the flexibility of the final product by modifying the molecular bonds of the polymer. Typically, the polymer molecule is held together by secondary valence bonds. The plasticizer replaces some of these bonds with plasticizer-to-polymer bonds, thus aiding movement of the polymer chain segments.

As used herein, a "xanthene" or "xanthene-based" molecule refers to an unmodified xanthene molecule or a derivative compound with a xanthene ring structure, as shown below. Xanthene ($CH_2(C_6H_4)_2O$) (dibenzopyran, tricyclic), a yellow organic heterocyclic compound, has the following chemical structure:

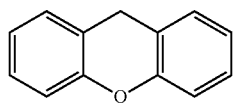 [SMILES: c1ccc2c(c1)Cc1ccccc1O2]

It is soluble in ether, and its melting point is 101-102° C. and its boiling point is 310-312° C. Xanthene is commonly used as a fungicide and is also a useful intermediate in organic synthesis. The xanthene molecule can be halogenated (F, Cl, Br, I). Halogenated xanthene structures may include, for example, mono-fluoro, di-fluoro, tri-fluoro, or tetra-fluoro-fluoresceins; mono-chloro, di-chloro, tri-chloro, tetra-chloro-fluorescein; mono-bromo, di-bromo, tri-bromo, or tetra-bromo-fluoresceins; or mono-iodo, di-iodo, tri-iodo, or tetra-iodo-fluoresceins, and mixtures thereof. Additionally, mixed halogenated xanthenes structures such as tetra-bromo-tetra-chloro-xanthene (e.g., Drug & Cosmetic (D&C) Red No. 27), are also contemplated.

Section II

Description

As the general public develops a wider social awareness of so-called "green" technologies and a desire to purchase products made from renewable materials, manufacturers are facing a challenge to try to respond to this consumer demand. Moreover, governmental requirements increasingly mandate the use of renewable or reusable materials in certain classes of disposable products has spurred a need to develop better and more innovative ways to deal with waste. In recent years manufacturers of plastic or thermoplastic products or materials have shown increasing interest in polylactic acid (PLA) polymers, which are an important, naturally occurring, renewable resource material that is inherently biodegradable. Since the material can be thermally processed into film, fibers, and molded parts, these polymers are a potential raw material replacement for polyolefins and other thermoplastic resins in consumer product and other applications. Manufacturers are seeking new ways to incorporate more recyclable or natural and biodegradable materials into otherwise conventional polymer-based products. Due to polylactic acid being both a sustainable and biodegradable or compostable polymer, interest grows in leveraging this "green" technology for a variety of uses, such as packaging, bottles, and disposable use articles.

The composting and biodegradation properties of semi-crystalline versus amorphous PLA materials differ. It is understood that the biodegradation kinetics of polylactic acid molecules are faster in the breaking down of amorphous regions and significantly slower in the breakdown more crystalline regions (Hideto Tsuji and Yoshito Ikada., J. Appl. Polym. Sci. 63: 855-863, 1997). Hence, it would be highly desirable to make essentially all of the polylactic acid be in an amorphous phase to increase the biodegradation kinetics of the polylactic acid waste. The composition according to the present invention describes such an essentially amorphous polylactic acid material.

In the past, the shortcoming associated with highly amorphous polymers is typically that the materials tended to be much weaker in strength/toughness compared to a more crystalline sample of the polymer. We have been able to overcome this disadvantage. The polylactic acid of the present invention can be actually stronger or tougher than control samples of semi-crystalline PLA polymer. This feature is a unique and unexpected finding of this inventive composition. In other words, materials of the present composition are both highly amorphous and yet surprisingly tougher than their analogue semi-crystalline control materials. These properties provide an ideal polymer composition to meet the application needs such as describe above.

A

In the past polylactic acid has been used as a specialty medical polymer at very high costs (>$10.00/g). Recent advances in polymer synthesis, and the use of renewable resources and agricultural waste products as feedstock's have made the production of this material at commodity prices possible. The literature on the polyester polymers derived from lactic acid can be somewhat confusing because there are several different methods for naming these polymers. Frequently, the abbreviation PLA refers not only to polymers derived from the "L" isomer of lactic acid (1) but also a mixture of the "L" isomer and the "D" isomer (2).

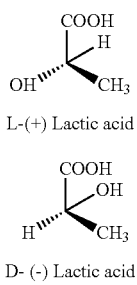

1

L-(+) Lactic acid

2

D- (-) Lactic acid

In addition, some workers have named poly(lactic acid) polymers as polylactides because these polymers were prepared from "lactide" (3), the cyclic "dimer" of L-(+) lactic acid.

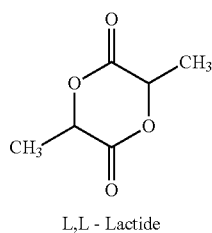

3

L,L - Lactide

Unless stated otherwise, PLA will refer generically to all polylactic acid polymers.

L-(+)-lactic acid is obtained by fermentation of inexpensive sources of glucose such as potato wastes, cheese whey permeate, or corn. The fermentation-derived L-lactic acid, however, is difficult to purify from all of the other carbohydrate by-products and bacterial cell breakdown products. The D-isomer of lactic acid is difficult to obtain, but researchers are exploring methods to genetically engineer bacteria to produce this isomer. The racemic mixture of lactic acid is synthesized from acetaldehyde. At this time, the racemic mixture is cheaper than the L-isomer which in turn is considerably cheaper than the D-isomer.

High molecular weight poly(L-lactic acid) is prepared by heating the lactide 3 in the presence of tin, lead, antimony or zinc catalysts, especially tetraphenyl tin[4] or stannous octoate (2-ethylhexanoate)[3a,b,d,5]. If the lactide is rigorously purified to remove water and trace of acids, high molecular weight poly(L-lactic acid) is obtained.

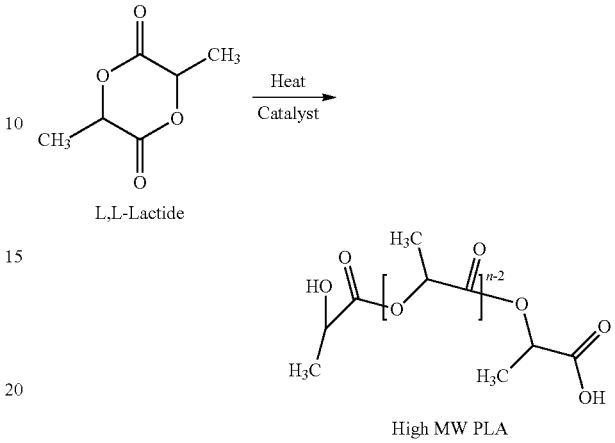

L,L-Lactide

High MW PLA

The resulting poly(L-lactic acid) [or poly(D-lactic acid) if D-lactic acid is used] is an isotactic, hydrophobic, brittle, tough polymer which becomes rubbery around 55-65° C. ($T_g$). It is semi-crystalline (37%) with a broad range of melting points (Tm) from 173-215° C. Poly(D,L-lactic acid) is reported to be totally amorphous, atatic, inelastic, and glassy with a softening point of 53° C.

B

Although some polymers may be completely amorphous, the morphology of most polymers is semi-crystalline. That is, they form a combination of crystalline and amorphous portions with the amorphous regions surrounding the crystalline areas. The mixtures of small crystals and amorphous material melt over a range of temperature instead of at a single melting point. The crystalline material tends to have highly ordered and regular structures formed by folding and stacking of the polymer chains. The amorphous structure, in contrast, shows no long range order, and have molecular chains are arranged randomly and in long chains which twist and curve around one-another, making large regions of highly structured morphology unlikely.

The highly ordered crystalline structure and amorphous morphology of certain polymer materials determine the differing behaviors of the polymer. An amorphous solid is formed when the chains have little orientation throughout the bulk polymer. The glass transition temperature ($T_g$) is the point at which the polymer hardens into an amorphous solid. The glass transition temperature of a polymer is an important factor in its physical properties and behavior for certain desired uses. As the temperature of a polymer drops below its $T_g$, the polymer behaves in an increasingly brittle manner; while, as the temperature rises above the $T_g$, the polymer becomes more viscous-like. In general, polymers with $T_g$ values of well below room temperature (~20° C.) define the domain of elastomers, and those with values above room temperature define rigid, structural polymers.

The $T_g$ can influence the mechanical properties of the polymeric material; in particular, the response of the material to an application of a force, namely: elastic and plastic behaviors. Elastic materials will return to their original shape once the force is removed. Plastic materials will deform fluidly and not regain their shape. In plastic materials, flow is occurring, much like a highly viscous liquid. Most materials demonstrate a combination of elastic and plastic behavior, exhibiting plastic behavior after the elastic limit has been exceeded. For example, polyvinyl chloride (PVC) has a $T_g$ of 83° C., making it good, for example, for cold water pipes, but unsuitable for hot water. PVC also will always be a brittle solid at room temperature. Adding a small amount of plasticizer to PVC can lower the $T_g$ to about −40° C. This addition renders the PVC a soft, flexible material at room temperature, ideal for applications such as garden hoses. A plasticized PVC hose can, however, become stiff and brittle in winter. In this case, as in any other, the relation of the $T_g$ to the ambient temperature is what determines the choice of a given material in a particular application.

In most polymers, the combination of crystalline and amorphous structures forms a material with advantageous properties of strength and stiffness. According to the present invention, while in furtherance of the work described in U.S. patent application Ser. No. 11/974,369, and Ser. No. 11/974,393, the content of which are incorporated herein by reference, we have discovered that xanthene or xanthene-based compounds can impart significant plasticizing properties to a variety of crystalline or semi-crystalline thermoplastic polymer materials with a crystalline level of more than about 14%. Examples of suitable xanthene-based compounds include xanthene dyes (e.g., xanthene base structure of fluorescein systems). Xanthene dyes are a class of dyes which includes fluoresceins, eosins, and rhodamines. They fall into three major categories: the fluorenes or amino xanthenes, the rhodols or aminohydroxyxanthenes, and the fluorones or hydroxy-xanthenes. Lillie, H. J. CONN'S BIOLOGICAL STAINS, p. 326 (Williams & Wilkins, 9th ed. 1977). Xanthene dyes tend to be fluorescent, yellow to pink to bluish red, brilliant dyes. The xanthene structure can have at least one functional R group, where R is hydrogen or halogen.

According to embodiments of the invention, xanthene and/or xanthene dyes can be incorporated into the thermoplastic polymer matrix by melt-mixing to enhance the physical plasticity of the resultant composition. Typically, the molten mixture is heated to a temperature of between about 140° C. and 280° C. This temperature can range from about 150° C. or 180° C. to about 230° C., 250° C. or 265° C., depending on the melting temperatures of specific thermoplastic polymers.

Nonetheless, according to the present invention, not all xanthene-based structures function well as a plasticizer. We have found that xanthenes-based compounds with ketone or carboxylic acid analogues (e.g., xanthone and xanthene-carboxylic acid) do not work as well as others since they appear not to impart good plasticizing characteristics, but rather can make the polymer material very brittle, even worse than a control sample of the original thermoplastic polymer material.

According to the present invention, the starting thermoplastic polymer can be a semi-crystalline polymer material with a minimal crystalline content of about 14% up to about 87% by weight of the polymer. Typical the polymer material has a crystalline content that can range from about 14% up to about 87% by weight; more typically a crystalline level of about 14% to about 25%. The plasticizing compound with a xanthene-based molecular structure can be in an amount from about 1000 ppm to about 6000 ppm. Typically, the plasticizing compound with a xanthene-based molecular structure can be present in an amount from about 3000 ppm to about 5000 ppm, inclusive.

The starting thermoplastic polymer, according to the present invention, has a crystalline phase, and an amorphous phase in a ratio range of about 14-87:86-13 respectively (desirably, about 25:75 crystalline phase: amorphous phase). The crystalline phase of the composition comprising the starting polymer with the xanthene or xanthene-based structure is reduced by an amount of about 40% up to about 99% relative to the percentage of crystalline phase of an identical composition absent the plasticizing compound with xanthene-based molecular structure.

In the crystallization process, it has been observed that relatively short chains organize themselves into crystalline structures more readily than longer molecules. Therefore, the degree of polymerization (DP) is an important factor in determining the crystallinity index of a polymer. Polymers with a high DP have difficulty organizing into layers because they tend to become tangled. Low molecular weight polymers (short chains) are generally weaker in strength. Although they are crystalline, only weak Van der Waals forces hold the lattice together. This allows the crystalline layers to slip past one another causing a break in the material. High DP (amorphous) polymers, however, have greater strength because the molecules become tangled between layers. In the case of fibers, stretching to 3 or more times their original length when in a semi-crystalline state produces increased chain alignment, crystallinity and strength.

Also influencing the polymer morphology is the size and shape of the monomers' substituent groups. If the monomers are large and irregular, it is difficult for the polymer chains to arrange themselves in an ordered manner, resulting in a more amorphous solid. Likewise, smaller monomers, and monomers that have a very regular structure (e.g. rod-like) will form more crystalline polymers.

The cooling rate also influences the amount of crystallinity. Slow cooling provides time for greater amounts of crystallization to occur. As used herein, "slow cooling" or "oven cooling" refers to a process in which one heats up an oven, such as in the present situation a vacuum oven, to its maximum temperature (e.g., 300° C.), place a sample in the oven, and turn off the heating element to allow the oven to gradually cool to ambient temperature. The oven cools down to room temperature over the course of several hours (e.g., 4-7 hrs.). To illustrate, for example, the maximum temperature is 225° C. (above the melting of PLA) and the cooling time is 4-5 hours. This cooling time is compared to the cooling with a rate of 10 C/min, which informs that the cooling time is about 22.5 minutes.

Fast cooling rates, on the other hand, such as rapid quenches, yield highly amorphous materials. Subsequent annealing (heating and holding at an appropriate temperature below the crystalline melting point, followed by slow cooling) will produce a significant increase in crystallinity in most polymers, as well as relieving stresses.

C.

To reiterate, the present invention, in part, relates to a thermoplastic polymer composition. The composition includes: a starting base semi-crystalline polymer with a minimal crystalline content of about 14% to about 25% by weight of the polymer, and a plasticizing compound with a xanthene-based molecular structure in an amount up to about 6000 ppm dispersed therein, and said blended composition mixture having a crystalline phase, and an amorphous phase in a ratio range of about 0-15:85-100, respectively when solid at ambient room temperature. The plasticizing compound is dispersed within the amorphous phase. The blended composition has a level of crystallinity of about at least 40-99% less than a starting control thermoplastic polymer not containing the plasticizing compound.

The composition has a ratio of about 0-15:85-100, respectively of the crystalline phase to amorphous phase when solid. The semi-crystalline polymer contains a crystalline content of about 0% to about 15% crystalline phase, 100% to about 85% amorphous state. The semi-crystalline polymer is selected from a group consisting: polyalkylcarboxylic acids, in particular polylactic acid.

The plasticizing compound has at least one R group, where R is hydrogen or a halogen. In other words, the xanthene-based molecular structure can be halogenated or mixed-halogenated. The plasticizing compound is present at about 3000 ppm to about 5000 ppm. The crystalline phase is reduced by an amount of about 40% to about 100% or up to about 300-400-500%, relative to the percentage of crystalline phase of an identical composition absent the plasticizing compound.

The composition can increase the toughness relative to an underlying thermoplastic polymer not having the plasticizing compound by about at least 40% or 50% or 60%. The composition increases in the stretch elongation tolerance relative to an underlying thermoplastic polymer not having plasticizing compound by about at least 40% or about 50%. The composition exhibits an increase in the strain at break said polymer relative to an underlying thermoplastic polymer not having plasticizing compound by at least 40%. The composition exhibits an increase in the stress at break said polymer relative to an underlying thermoplastic polymer not having plasticizing compound by at least 40%.

The composition exhibits faster biodegradation and composting kinetics compared to a control sample of the same polymer without the xanthene or xanthenes-based additive and yet is tougher than the control polymer without the xanthenes or xanthene-based additive. The composition is essentially amorphous and tougher than the control polymer without the xanthenes or xanthene-based additive.

According to another aspect, the invention discloses a method of plasticizing a crystalline-phase-containing polymer. The method involves: providing a starting thermoplastic polymer with about 14 to about 25% crystallinity index phase. The method comprises: providing in a mixture a starting polymer with about 14% to about 25% crystallinity and a plasticizing agent having a xanthene-based molecular structure present in an amount of up to about 5000-6000 ppm, of total composition; mixing said thermoplastic polymer and said plasticizing agent in a molten or liquid state between a temperature range of about 140° C. to about 300° C.—typically, about 140° C. or 150° C. up to about 285° C. or 290° C.; and dispersing uniformly said plasticizing agent throughout said molten mixture; and solidifying said molten mixture such that said xanthene-based molecular structure migrates into an amorphous phase. One may form an article from the molten mixture. The method may further include extruding or forming said molten mixtures into a solid when at about ambient room temperature. When solidified, the resulting solid exhibits a level of crystallinity that is at least 40% to about 100% or 500% less than original thermoplastic polymer without said plasticizing agent. The mixture is heated to a temperature of between about 170° C. and 280° C.

Section III

Practical Applications

In another aspect, the invention describes an article of manufacture that is fabricated with least in part with a thermoplastic polymer. The thermoplastic polymer has a semi-crystalline polymer matrix incorporating a plasticizer comprising a xanthene molecule or a compound with a xanthene-based molecular structure. The xanthene molecule or compound with a xanthene-based molecular structure is present in the polymer matrix in an amount of about 3000 ppm up to about 5000 or 6000 ppm. The xanthenes molecule or compound with a xanthene-based molecular structure is selected from an unmodified, halogenated, or mixed-halogenated xanthenes-based compound. The underlying original thermoplastic polymer is selected from a group consisting: polyalkylcarboxylic acids. The article can be a fiber or filament, or fiber-web made from an extrusion of said thermoplastic composition comprising a starting semi-crystalline polymer with a minimal crystalline content of about 14% by weight of the polymer, and a compound with a xanthene-based molecular structure in an amount up to about 5000-6000 ppm dispersed therein, and said blended final composition having a crystalline phase, and an amorphous phase in a ratio range of about 0-15:85-100, respectively when solid at ambient room temperature. The article may the form of a film, fiber, fiber web, absorbent pad, diaper, adult incontinence or feminine hygiene product, protective fabric, face-mask, medical drape, wiper, garment, and packaging article. In such an embodiment, the fiber can be part of a woven fabric. The fiber-web can form part of a nonwoven fabric. The article can be a laminate structure with a film layer made from an extrusion of the thermoplastic composition.

In general, according to the present invention, thermoplastic polymers compositions that have xanthene-based compounds incorporated tend to be tougher at a temperature range of about 30° C. to about 50° C., which appears to be an effect of lowering the crystalline content of the modified or plasticized polymer. Incorporation of the plasticizer compound into the thermoplastic polymeric composition can increase the relative toughness of the base or underlying thermoplastic polymer by about at least 20%. In certain embodiments, the toughness can be enhanced by as much as 20% up to about 50%. Strain at break of a xanthene containing polymer sample is increase compared to the control by at least 20% to 40%. The relative tolerance for elongation is improved by about at least 20%. This parameter can also be increased by about 20%, up to about 50%. The xanthenes containing thermoplastic material exhibits an increase in stress to break applied to pull apart the polymer by at least 20%, and up to about 50%.

With such properties, films, fibers, and fibers-webs formed from the present compositions tend to be more drapable and ductile. This characteristic would allow manufacturers to provide garments, covers, wrapping materials, or packages made with woven or nonwoven fabric materials made with such polymers to be more conformable and convey a softer texture to the touch. Garments may include, for example, overalls, gowns, drapes, footwear, gloves, or headwear. Also a more pliable quality of the polymer can result in a quieter film and less "crinkle in noise" when crumbled or crushed. Fibers and fabrics made from those fibers containing the xanthenes-based compounds would be softer and also more drapable. Thus for example, polypropylene nonwoven would be converted into a more polyethylene-like softer fabric (less harsh in feel). This property would be ideal for manufactured articles that incorporate nonwoven layers, especially for those that contact a consumer or user's skin, such as absorbent pads, feminine hygiene pads, diapers, or wash cloths and wipers. In particular, manufacturers can modify existing nonwoven technology and materials, for instance, co-formed fibers or hydroknit fibers, combined films, fibers and webs for laminate structures, such as sponbond, sponbond-meltblown-spunbond, sponbond-film-sponbond. A film can allow for micro-porous pore dimensions of about 10-50-100 microns. Other potential products may include injection or extrusion molded articles, for example, bladders or balloons, catheter tubing, or endotracheal tubes. Conventionally, such tubes and conduits have been made from rather rigid thermoplastic polymers, which may cause pain and tissue damage, if not inserted smoothly along the passageways in a patient's body. A more pliable material that is able to flex when contacting a bend, for instance, in the trachea or esophagus would avoid such injuries. Therefore the uniqueness of this invention is the ability to convert "harder polymers" into softer and more pliable films, fibers, webs made from the fibers, and/or laminate structures.

Section IV

Empirical

1. Materials

All chemicals and solvents were obtained from Sigma-Aldrich Chemical Company (Milwaukee Wis.) and used without further purification unless specified in the following section.

2. Analytical Methods

DSC

The samples were analyzed on a TA Instruments DSC Q 2000 (T-zero Cell) using the following experimental procedure:

Approximately 5 mg cut from the specimens were encapsulated in the DSC pans. The specimens were run in the temperature interval 20° C. to 200° C. with a heating/cooling rate of 10° C./min. The as-received solution cast materials and the materials melted and slowly cooled (cooling time 4-5 hours) in a vacuum oven were tested. All measurements were executed in an inert gas (He) atmosphere.

WAXS

The materials were analyzed on an X-ray diffractometer D-max Rapid from Rigaku Corp. equipped with a two dimensional (2-D) position sensitive detector. The measurements were executed in transmission geometry and Cu Kα radiation (λ=1.5405 Angstrom). The as-received solution cast materials, the materials obtained after melting and re-crystallization in the DSC pans (cooling rate 10° C./min) and the materials melted and slowly cooled (cooling time 4-5 hours) in a vacuum oven were tested.

DMA

Films with thickness ~0.25 mm were compression molded at 225° C. and cooled to room temperature with a rate of 10° C./min. Strips with lengths 10 mm and widths 3 mm were studied using Q800 instrument from TA Instruments. The samples were tested in tension/tension deformation mode. The experimental runs were executed in a temperature sweep mode in the range from −30° C. to +50° C. with a heating rate of 3° C./min, at constant frequency (2 Hz) and constant static force of 2.5N. The stress amplitude was ±10% of the static force.

Crystallinity Index

The crystalline content of any semicrystalline material can be computed from the crystallinity index[29]:

$$X\% = \frac{I_c}{I_t} = \frac{\int i_c k^2 dk}{\int i_t k^2 dk} \quad (1)$$

Where $I_c$ is the XRD intensity scattered from the crystalline portion of the material, $I_t$ is the total XRD intensity and k is the scattering vector with a magnitude k=4π sin θ/λ, (λ is the wavelength of the X-ray radiation and θ is the scattering angle).

3. Sample Preparation

Example 1

4,5-Dibromofluorescein (DBF, 5000 ppm) in polylactic acid

An amount of 1.0 gram polylactic acid (molecular weight Mn ~30,000; Mw ~55,000) was dissolved in 20 ml of chloroform at ambient temperature with stirring. The clear solution was separated into two equal 10 ml aliquots and to one of which was added 100 mg of dibromofluorescein and the mixture stirred to dissolve the dye. Both solutions were solvent cast by pouring into respective aluminum weighing pans (6 cm diameter×1 cm depth) and the solvent evaporated overnight (8-12 hrs.) in a fume hood. The films were then removed and analyzed.

Example 2

4,5-dichlorofluorescein (DCF, 5000 ppm) in polylactic acid

The procedure described in example 1 was repeated except that dichlorofuorescein was used.

Example 3

4,5-diiodofluorescein (DIF, 5000 ppm) in polylactic acid

The procedure described in example 1 was repeated except that diiodofluorescein was used.

Example 4

Xanthene (X, 5000 ppm) in polylactic acid

The procedure described in example 1 was repeated except that xanthene was used.

Example 5

Tributyl-o-acetylcitrate (TBAC, 5000 ppm) in polylactic acid

The procedure used in example 1 was repeated except that TBAC was used.

Example 6

4,5-Dibromofluoroscein (BDF, 2000 ppm) in polylactic acid

The procedure used in example 1 was repeated except that 40 mg of dibromofluoroscein was used.

Example 7

4,5-Dibromofluorescein (DBF, 7000 ppm) in polylactic acid

The procedure used in example 1 was repeated except that 350 mg of dibromofluoroscein was used.

4. Results

Figure 2:
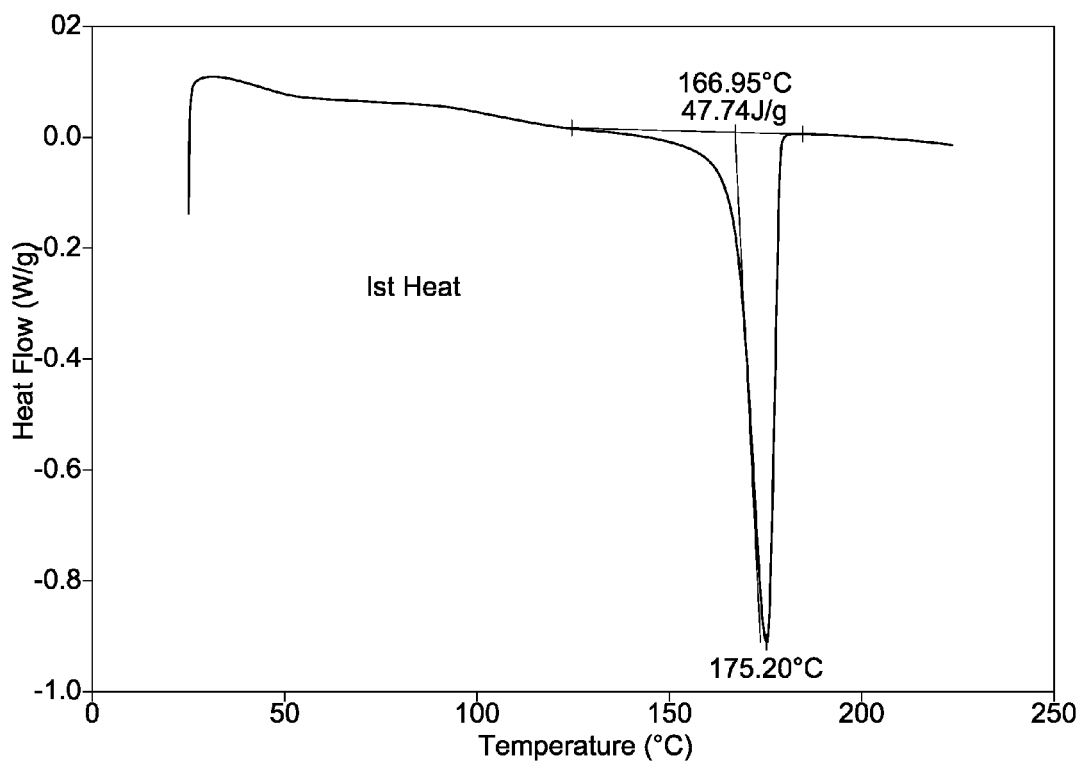
FIG. 2 shows a graph of the DSC curve of Example #1 (PLA+5000 ppm DBF—solution cast); first heat.
Figure 3:
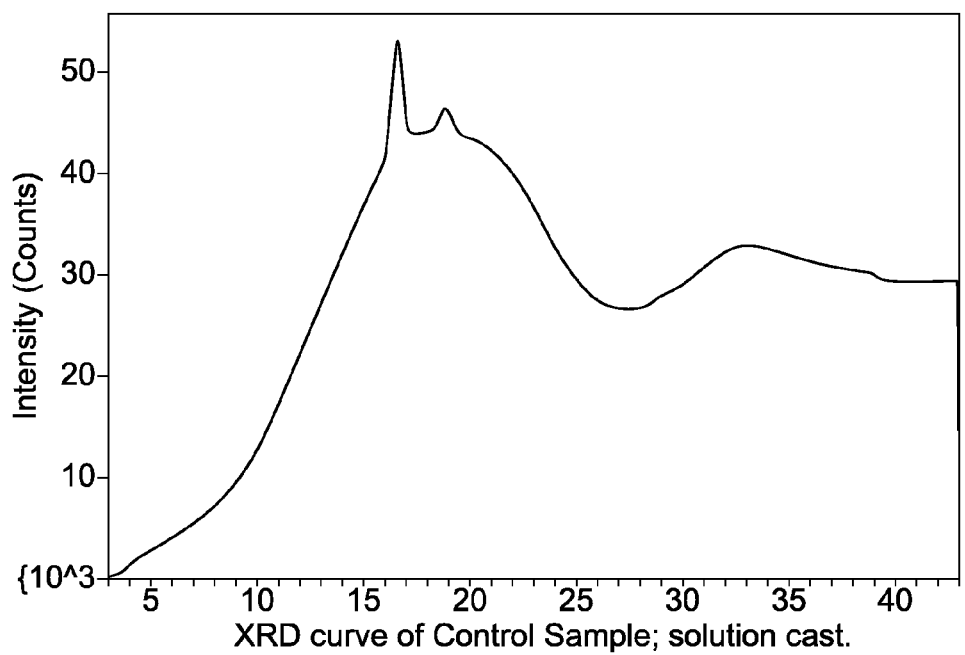
FIG. 3 is a graph of the XRD curve of Control Sample; solution cast.
Figure 4:
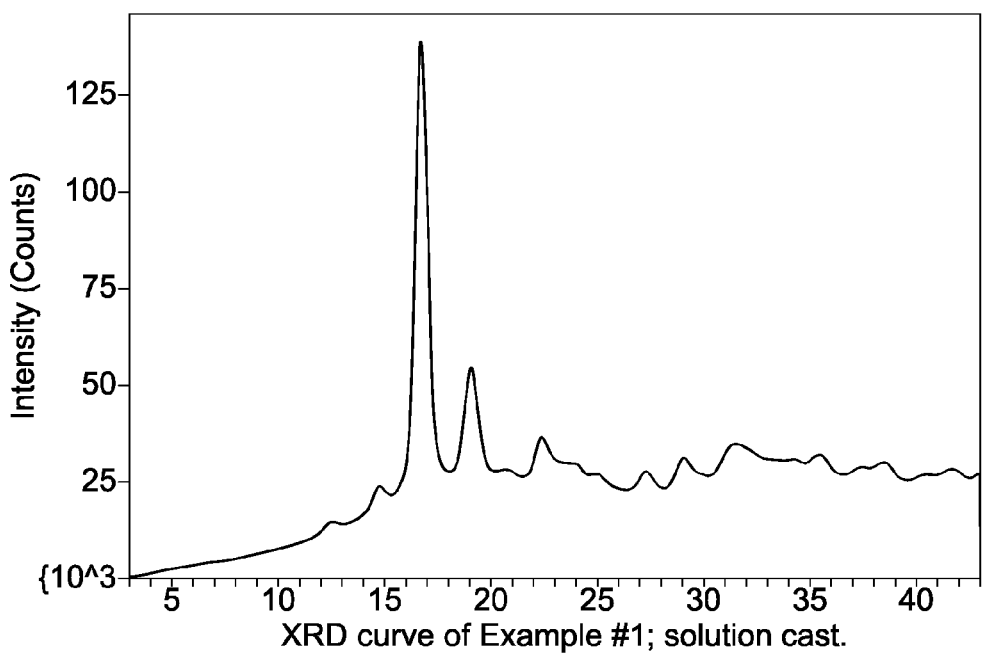
FIG. 4 is a graph of the XRD curve of Example #1; solution cast.

In FIGS. 1 and 2, the DSC heating curves—$I^{st}$ Heat of the two materials are drawn. Inspection of FIG. 1, shows that the glass transition process is clearly detectable for Sample#1, while it is quite smeared or indiscernible for Sample#2 in FIG. 2. Further, Sample#1 is characterized with a significant cold crystallization process, while Sample#2 is not. These results are indicative of relatively low crystallinity (as measure by its crystallinity index) content in Sample#1 (the solution cast control sample) and a much higher level of crystallinity (crystallinity index) in Sample#2 (the solution cast PLA+5000 ppm DBF). XRD results shown in FIGS. 3 and 4, confirm the DSC results. After fitting the experimental X-ray curves into crystalline and amorphous components it was found that the crystalline fraction is ~14% in Sample#1 vs. 52% in Sample#2, as summarized in Table 1.

TABLE 1

| Sample ID | X % after Solution Casting | X % after Cool 10° C./min | X % after Slow Cool |
| --- | --- | --- | --- |
| Control Sample PLA control | 14 | 25 | 87 |
| Example #1 PLA + 5000 ppm DBF | 52 | 0 | 85 |

Figure 5:
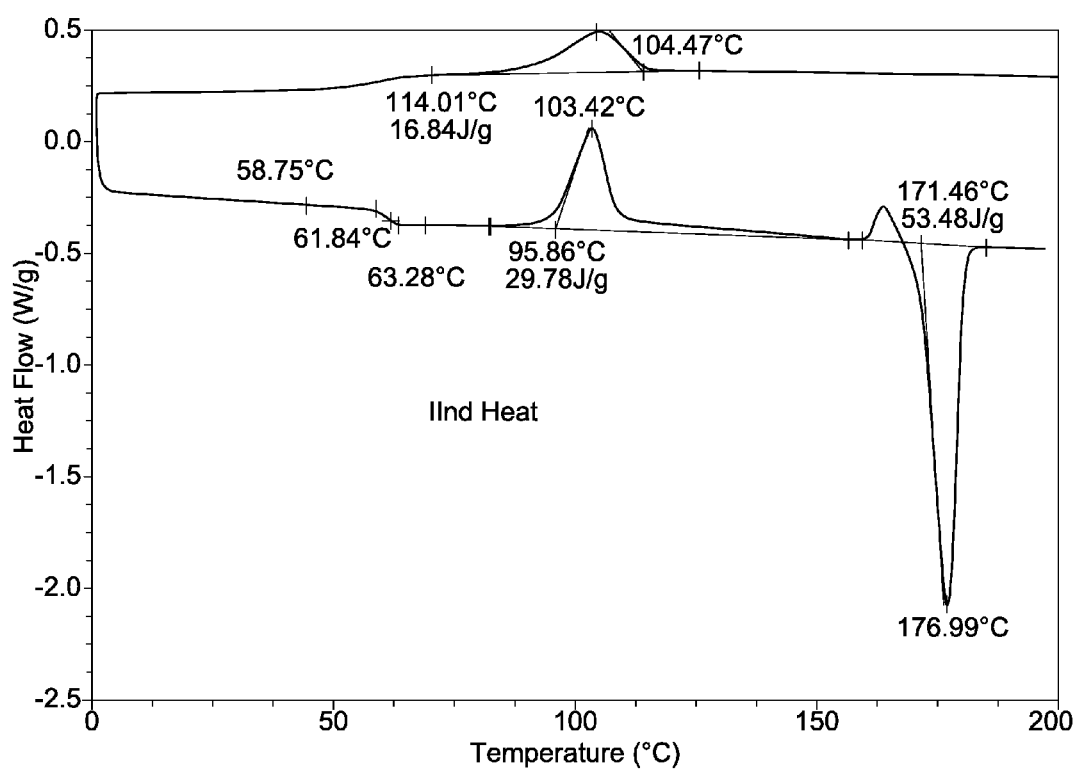
FIG. 5 is a graph of the DSC curve of Control Sample (PLA control); cooling and second heat.
Figure 6:
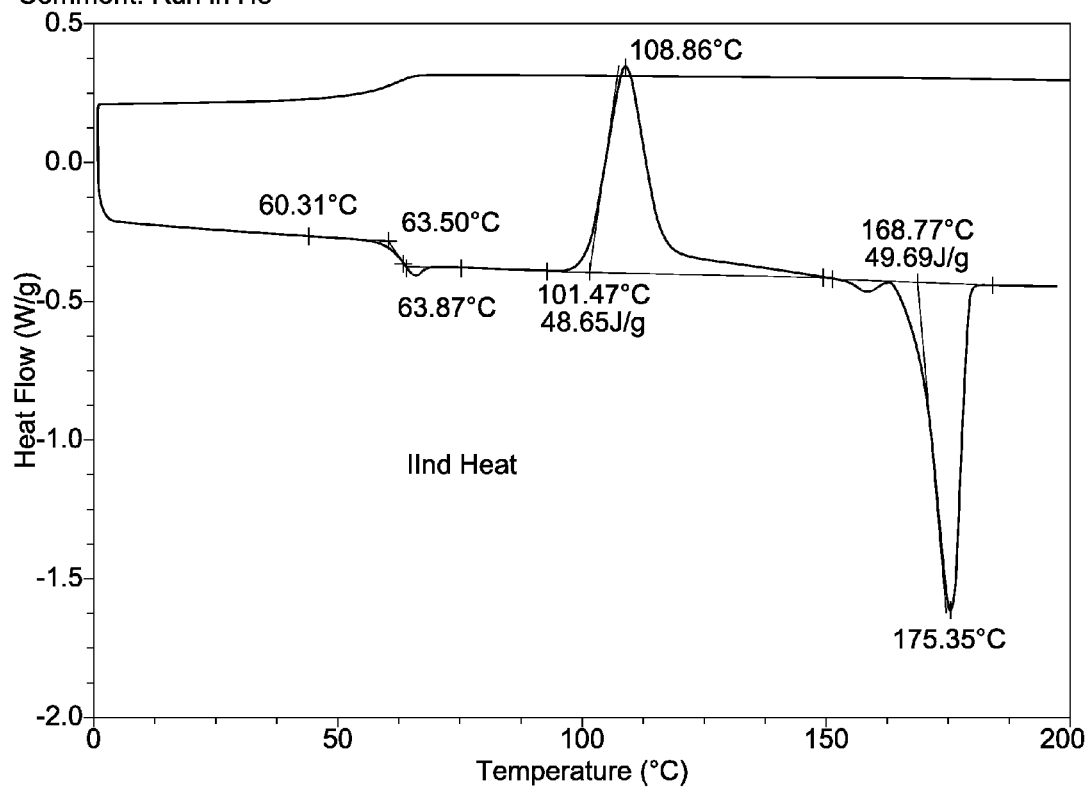
FIG. 6 is a graph of the DSC curve of Example #1 (PLA+5000 ppm DBF); cooling and second heat.
Figure 7:
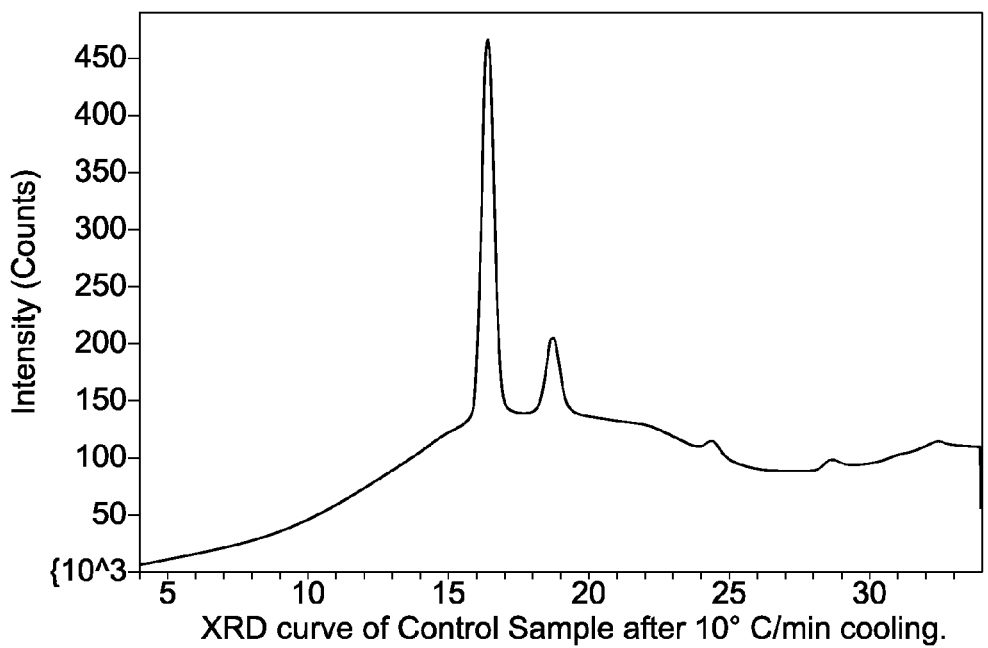
FIG. 7 shows a graph of the XRD curve of Control Sample after 10° C./min cooling.
Figure 8:
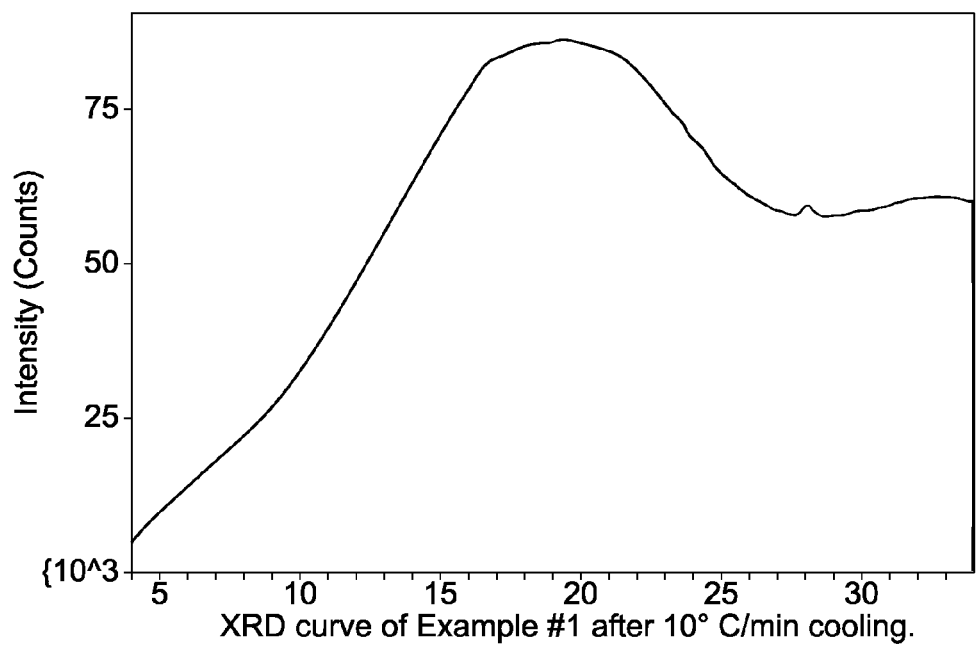
FIG. 8 shows a graph of the XRD curve of Example #1 after 10° C./min cooling.
Figure 9:
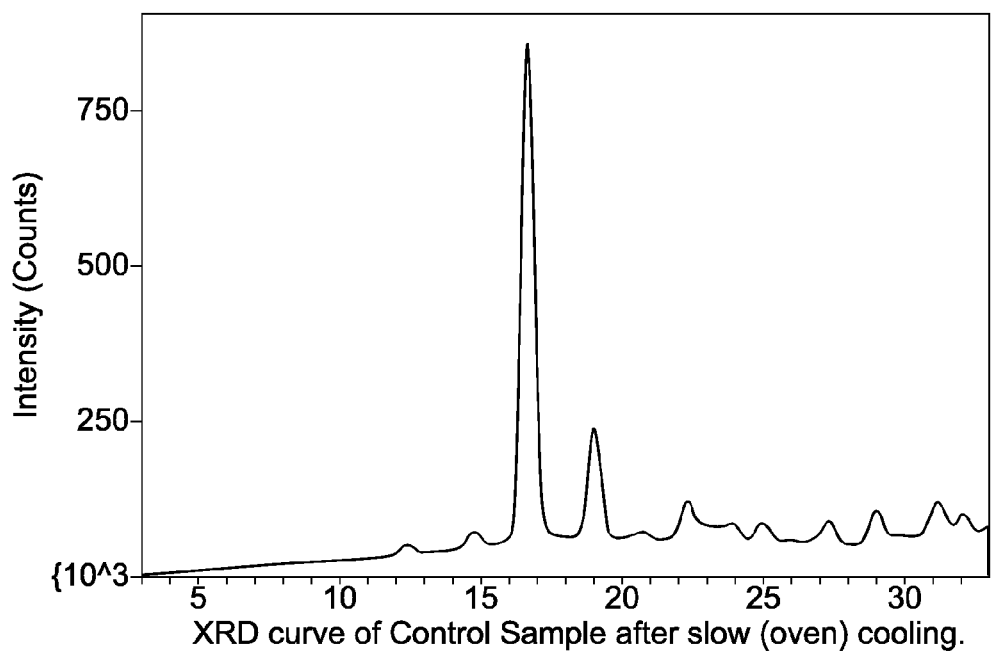
FIG. 9 shows a graph of the XRD curve of Control Sample after slow (oven) cooling.
Figure 10:
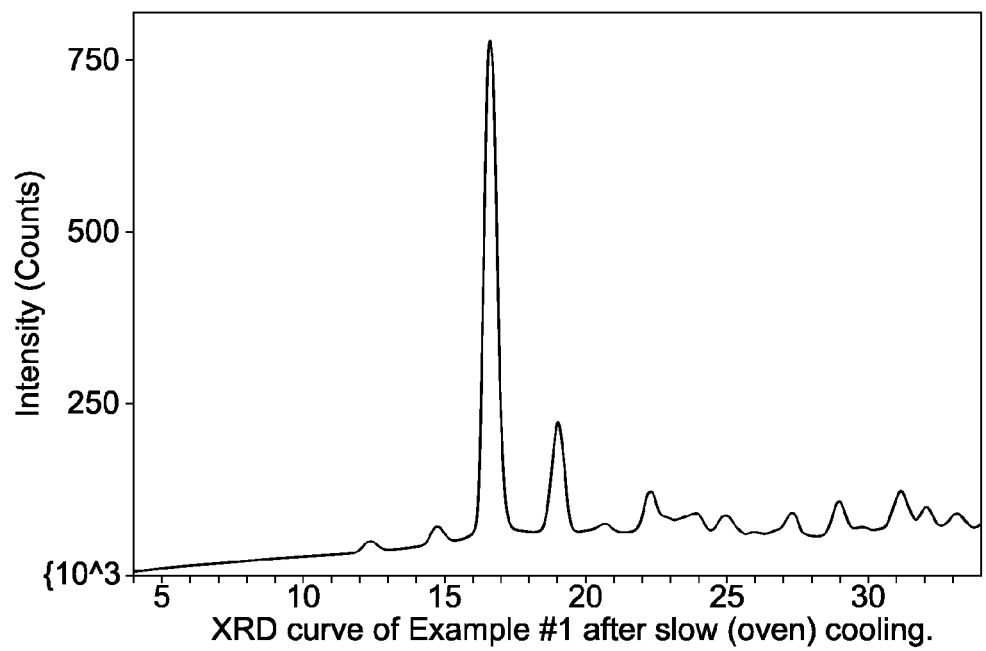
FIG. 10 shows a graph of the XRD curve of Example #1 after slow (oven) cooling.

These results would tend to suggest that the DBF acts as a nucleating agent in the PLA matrix. The cooling DSC curves and the $II^{nd}$ Heat curves (FIGS. 5 & 6), however, indicate exactly the opposite. The molten Sample#1 crystallizes partially after cooling with a rate of 10° C./min, while Sample#2 appears to lack any crystallinity under the same conditions. The XRD curves (FIGS. 7 & 8) confirm the DSC results and the fitting gives ~25% crystallinity index vs. ~0% in Table 1. After melting and slow cooling both materials are characterized with a very high crystalline index content as illustrated by FIGS. 9 and 10, and Table 1.

Other Xanthene Compounds

Other xanthenes compounds were tested in the PLA. Table 2, below, reports that all the xanthenes compounds have the similar unique effect on PLA as the DBF, however DBF appears to have the largest effect. The TBAC sample was made to compare the xanthenes to the traditional plasticizer. The results show that TBAC reduces the crystallinity (as measured by its crystallinity index) after the cool cycle, but not as great as the xanthenes.

TABLE 2

| | Percent Crystalline Index | | |
| --- | --- | --- | --- |
| Sample | X % after solution casting | X % after cool 10 C./min | X % after Slow cool |
| Control Sample PLA control | 14 | 25 | 87 |
| Example #1 PLA + 5000 ppm DBF | 52 | 0 | 87 |
| Example #2 PLA + 5000 ppm X | 38 | 14 | 85 |
| Example #3 PLA + 5000 ppm DCF | 43 | 11 | 86 |
| Example #4 PLA + 5000 ppm DIF | 41 | 4 | 83 |
| Example #5 PLA + 5000 ppm TBAC | 14 | 15 | N/A |
| Example #6 PLA + 2000 ppm DBF | 6 | 8 | N/A |
| Example #7 PLA + 7000 ppm DBF | 5 | 4 | N/A |

Explanation of the Analysis of the XRD Curve

Figure 11:
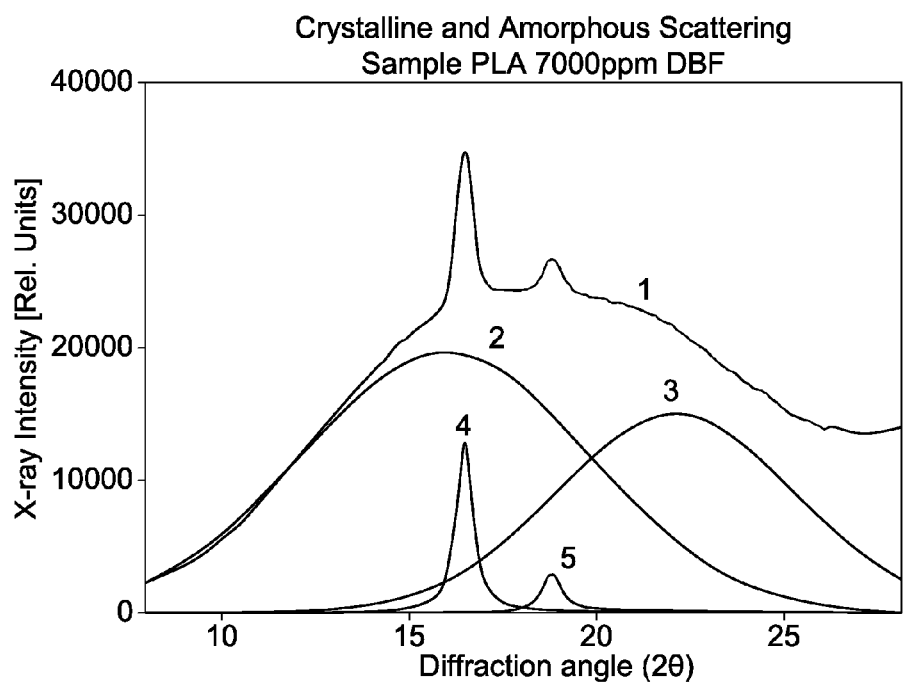
FIG. 11 is a graph of the XRD experimental curve of Example #7, after cooling at 10° C./min (curve #1). Curves #2 and #3 are two amorphous halos and curves #4 and #5 are two crystalline peaks.

By way of illustration, the XRD experimental curve of Example #7, PLA containing 7000 ppm DBF, after slow cooling at 10° C./min (curve #1) is shown in FIG. 11. The curve has been analyzed to show the composition of both crystalline and amorphous components of the PLA polymer. Curve #1 in FIG. 11 represents the composite curve of the other curves #2-5. Curves #2 and #3 are two amorphous halos, and curves #4 and #5 are two crystalline peaks. The crystalline index of the resulting material from Example #7 is reduced by a factor of 4-5 when compared to the crystallinity of its starting polymer material. It is believed that this results from the incorporation of DBF to generate an increased amorphous state content in the material. More thorough blending of the xanthenes-like molecules throughout the starting polymer materials may generate even better results.

The DMA Study of the Storage Modulus of PLA Control Versus PLA with 5 Wt % DBF with Temperature Films with thickness ~0.25 mm were compression molded at 225° C. and cooled to room temperature with a rate of 10° C./min. Strips with lengths 10 mm and widths 3 mm were studied using Q800 instrument from TA Instruments. The samples were tested in tension/tension deformation mode. The experimental runs were executed in a temperature sweep mode in the range from −30° C. to +50° C. with a heating rate of 3° C./min, at constant frequency (2 Hz) and constant static force of 2.5N. The stress amplitude was ±10% of the static force.

Figure 12:
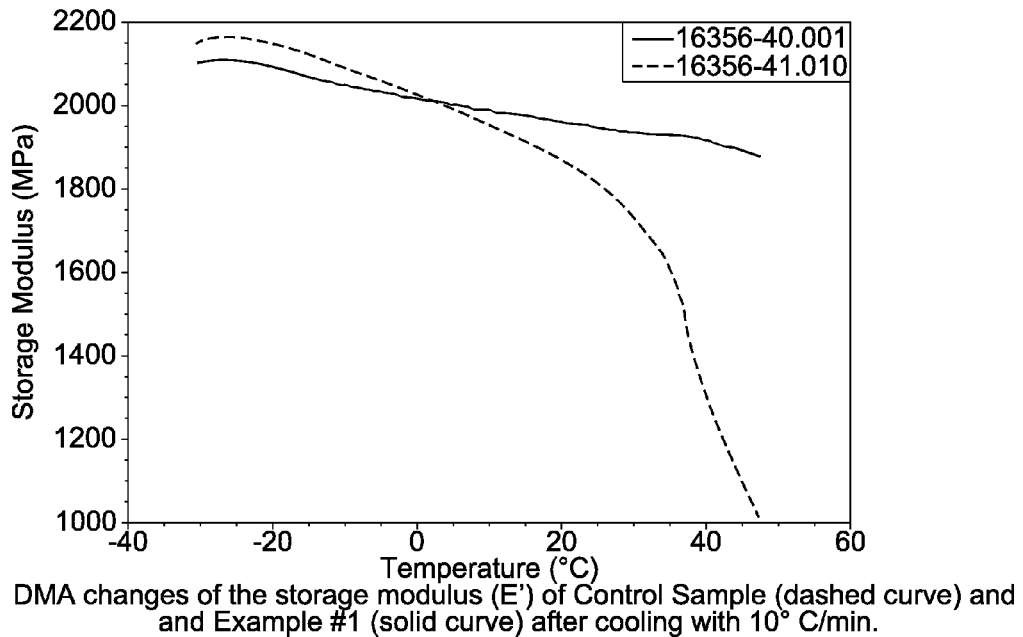
FIG. 12 shows the DMA changes of the storage modulus (E') of Control Sample (dashed curve) and Example #1 (solid curve) after cooling with 10° C./min.

The DMA analysis of the storage modulus of PLA control film versus PLA containing 5000 ppm DBF over temperature shows a most unusual and unique property. FIG. 12 shows the remarkable curves. It would appear that the DBF sample maintains good storage modulus across the temperature range (−30° C. to 50° C.) without softening. This is surprising considering it is essentially amorphous and should soften with increasing temperature. In contrast, the control PLA softens dramatically at around 10° C. with a large decrease in storage modulus from about 30° C. and higher. This is surprising as the sample that has some crystallinity (approximately 25% based on its crystallinity index). Clearly, the results are the opposite of what one skilled in the art would expect and predict. While the mechanism of the action of DBF is not fully understood, it is thought that the DBF is acting, in some manner, as a mild chain linking agent of the amorphous polymer chains resulting in not allowing the chains to move about with the same freedom of motion that the control amorphous chains express.

TABLE 3

Storage Modulus at Different Temperatures

| Sample ID | Temperature | | | | | | | | | | | |
|---|---|---|---|---|---|---|---|---|---|---|---|---|
| | −25° C. | −10° C. | 0° C. | 5° C. | 10° C. | 15° C. | 20° C. | 25° C. | 30° C. | 35° C. | 40° C. | 45° C. |
| E' - PLA Control | 2.2 | 2.1 | 2.03 | 1.99 | 1.95 | 1.91 | 1.87 | 1.82 | 1.73 | 1.61 | 1.3 | 1.09 |
| E' - PLA + 5000 ppm DBF | 2.1 | 2.05 | 2.02 | 2 | 1.99 | 1.97 | 1.96 | 1.945 | 1.93 | 1.93 | 1.92 | 1.89 |

Note:
The values of the storage modulus in Table II are in MPa × $10^{-3}$.

Analysis of the Stress-Strain (Toughness) of the Films Samples
Sample ID
Control Sample—PLA Control 1 (Solution Cast)
Example #1—PLA+5000 ppm Di-Bromo Fluorescein (DBF—solution cast)
Preparation of the Film Samples for Dma Analysis Films with a thickness of ~0.25 mm were compression molded at 225° C. and cooled to room temperature with a rate of 10° C./min. (The oven of the DMA instrument was utilized for the controlled cooling.) Strips with lengths 20 mm and widths 3 mm were studied using Q800 instrument from TA Instruments. The samples were tested in Stress-Strain deformation mode at temperatures 25° C. and 40° C. The applied force was increase with a rate of 2 N/min until the break of the tested specimens.

Figure 13:
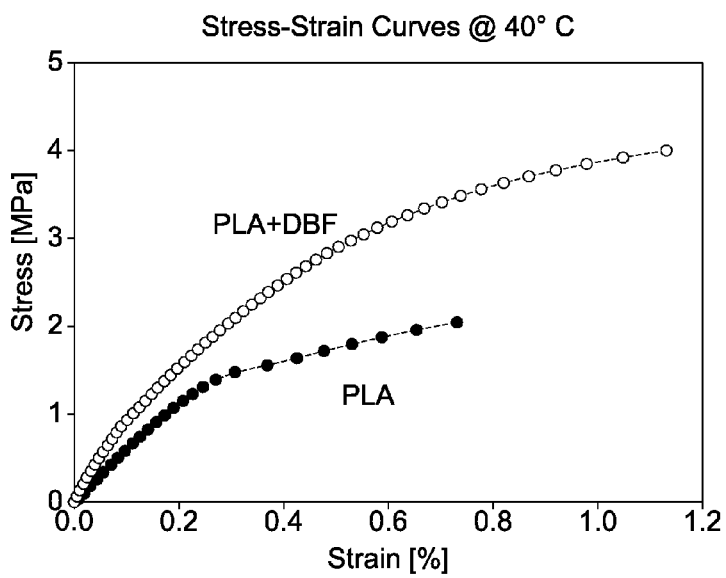
FIG. 13 shows the stress-strain curves @ 40° C. of Control Sample (PLA and 10° C./min cooling; solid circles) and Example #1 (PLA+5000 ppm DBF and 10° C./min cooling; open circles).

In FIG. 13 are plotted the stress-strain curves of the two materials at temperature 40° C. The results indicate that the modified material is characterized with higher elongation and stress at break. The relevant parameters are summarized in Table 4.

TABLE 4

Deformation @ 40° C.

| Sample ID | $\epsilon_b$[%] | $\sigma_b$[MPa] | W[MPa] |
|---|---|---|---|
| PLA | 0.73 | 2 | 1.1 |
| PLA + 500 ppm DBF | 1.13 | 4 | 3.3 |

Note:
In Table 4 $\epsilon_b$ is the strain at break; $\sigma_b$ is the stress at break and W is the toughness (the area under the respective curves).

Overall, the results from the XRD and DSC studies indicate that the addition of a relatively small amount (e.g., about 5000 ppm) of DBF can affect significantly the crystallization behavior of PLA. The preparation of the materials by solution casting (similar in many respects to slow cooling) suggests that the DBF acts as a nucleating agent and increases significantly the crystallinity content (as measure by its crystallinity index, X %). However after melting and cooling with 10° C./min the DBF completely suppresses the crystal formation. Slow (oven) cooling is not affected by the presence of DBF. The other xanthenes also show this unique effect on PLA, but are not as functionally effective as the DBF system.

A surprising observation was made when the films were analyzed by DMA. The DBF-PLA films, while essentially amorphous, had essentially no change in their storage modulus on heating from −10° C. to 30° C. Whereas the control PLA films, with approximately 25% crystallinity index, lost their storage modulus with increasing temperature with a steep slope after 20° C. and higher. This is truly the opposite that anyone skilled in the art would have predicted based on the literature of semi-crystalline versus amorphous polymers.

After DMA analysis the samples were placed in chloroform at ambient temperature to see if they would dissolve in the solvent. If the DBF had cross-linked the polymer chains it would have made the films less likely to dissolve in the solvent. Both film samples were found to dissolve completely in the solvent showing that the polymer chains were not cross-linked This makes the action of the DBF quite unique in its ability to suppress crystallization but make the essentially amorphous PLA film tougher, which is a surprising or unexpected, and unique finding.

While the mechanism is not fully understood, it is believed that the DBF is acting as a mild chain linking agent between the amorphous polymer chains restricting their motion as compared to the control amorphous polymer chains. Although some literature suggest that the addition of certain known cross-linking agents can strengthen polylactic acid, with the higher the concentration of crosslinker added the stronger the material, but xanthenes are not known to be cross-linkers. Xanthene or xanthene-like molecules do not have any suitable chemical sites that could participate in chemical crosslinking With such unique properties (essentially amorphous and strong) the polymer composition of the present invention potentially may leads to its use in various applications. For instance, to fabricate articles that exhibit or are desired to have higher biodegradation/composting rates due to the essentially amorphous nature of the composition. Alternatively, it may be used for essentially amorphous polymer articles and yet tougher than the control or base polymers in the temperature range from 30 to 50° C. The article of manufacture can be a film, a fiber, woven fibers, or nonwoven fiber web, absorbent articles (e.g., wipers, diapers, adult incontinence products, feminine pads), garments, protective fabrics and suits (e.g., surgical gowns or drapes, work overalls, dust or chemical protective outfits), wrapper or packaging materials or articles (e.g., diaper bag), face-masks, medical drapes, endotracheal tube, catheters, bladders or balloons, or any other item that may require a certain degree of flexibility or pliability and yet tougher.

The present invention has been described both generally and in detail by way of examples and the figures. Persons skilled in the art, however, can appreciate that the invention is not limited necessarily to the embodiments specifically disclosed, but that substitutions, modifications, and variations may be made to the present invention and its uses without departing from the spirit and scope of the invention. Therefore, changes should be construed as included herein unless the modifications otherwise depart from the scope of the present invention as defined in the following claims.

We claim:

1. A thermoplastic polymer composition comprising: a semi-crystalline polymer with a minimal crystalline content of about 14% to about 25% by weight of the polymer, and a plasticizing compound with a xanthene-based molecular structure in an amount up to about 6000 ppm dispersed therein, said composition having a level of crystallinity at least 40-99% less than said semi-crystalline polymer when solid at ambient room temperature, wherein said semi-crystalline polymer is selected from a group consisting of polyalkylcarboxylic acids.

2. The thermoplastic polymer composition according to claim 1, wherein said composition can increase the toughness relative to a control thermoplastic polymer not having said plasticizing compound by about at least 40% to about 60%.

3. The thermoplastic polymer composition according to claim 1, wherein said composition increases in the stretch elongation tolerance relative to a control thermoplastic polymer not having plasticizing compound by about at least 40% to about 50%.

4. The thermoplastic polymer composition according to claim 1, wherein said composition exhibits an increase in the strain at break said polymer relative to a control thermoplastic polymer not having plasticizing compound by at least 40%.

5. The thermoplastic polymer composition according to claim 1, wherein said composition exhibits an increase in the stress at break said polymer relative to a control thermoplastic polymer not having plasticizing compound by at least 40%.

6. The thermoplastic composition according to claim 1, wherein said composition exhibits faster biodegradation and composting kinetics compared to a control polymer without the xanthene or xanthenes-based additive.

7. The thermoplastic composition according to claim 1, wherein said composition is essentially amorphous.

8. A film made from an extrusion of the thermoplastic composition according claim 1.

* * * * *